United States Patent [19]

Chamberlin, Sr.

[11] Patent Number: Plant 6,006

[45] Date of Patent: Sep. 8, 1987

[54] PLUM TREE, "HOWARD SUN"

[75] Inventor: Thomas O. Chamberlin, Sr., Visalia, Calif.

[73] Assignee: H. P. Metzler & Sons, Del Rey, Calif.

[21] Appl. No.: 802,360

[22] Filed: Nov. 27, 1985

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is characterized by fruit which has a deep blue, almost black skin color and which possesses a yellow-colored flesh, the fruit having excellent shipping and storage qualities.

1 Drawing Figure

BACKGROUND OF THE NEW VARIETY

The present invention relates to a new and distinct variety of plum tree denominated varietally as the "Howard Sun", and more particularly to such plum tree which bears a dark blue to almost black-colored plum which is heart shaped in appearance, possesses excellent storage and handling qualities and is ripe for picking approximately Aug. 25 through 28. The "Howard Sun" Plum Tree is further characterized by having a yellow flesh and being nearly freestone by nature.

For decades, the applicant has endeavored to upgrade the quality of fruit which is produced by his employer, H. P. Metzler & Sons, of Del Rey, Calif. Accordingly, the applicant is constantly on the alert to locate any new varieties that may appear as seedling trees on any of the employer's several farms. As a part of his regular duties, the applicant has, as a regular practice, germinated thousands of random seeds, grown the resultant seedlings to maturity, and thereafter carefully studied the pomological characteristics of the progeny to determine whether the seedlings have produced any new and distinct varieties. The present variety of plum tree is a product of this procedure.

The plum tree of the present invention is characterized as to novelty by a ripening date of approximately Aug. 25 through 28 at Del Rey, Calif., and producing a fruit that is firm; resists bruising; which handles and ships very well; and displays excellent cold storage characteristics. In addition, the subject tree evidences the characteristic of being self-pollinating, and appears capable of aiding other plum trees near it to pollinate.

ORIGIN

The "Howard Sun" variety of plum tree was a chance seedling which resulted from the germination by the applicant of large number of seeds which were procured from the H. P. Metzler & Sons Ranch No. 5, located near Del Rey, Calif. The subject seeds were germinated and originally planted in the H. P. Metzler & Sons Nursery in early 1980. The chance seedling produced its first fruit in 1982. At that time, the seedling was identified as having the desired characteristics of producing fruit late in the season which had the qualities the applicant was seeking. Early in the fall of 1982, buds were collected from the parent tree and were thereafter dormant budded onto test seedlings which were subsequently planted in the H. P. Metzler & Sons Testing Block early in the spring of 1983. These budded test seedlings bore their first fruit in the summer of 1984.

This first asexual progagation resulted in progeny being produced which were found to possess the same distinctive characteristics as the original seedling.

BRIEF DESCRIPTION OF THE DRAWING

The accompanying drawing is a color photograph of a characteristic twig bearing typical leaves, several plums showing their external coloration sufficiently mature for harvesting and shipment, two mature plums of the color when matured on the trees, a plum halved transversely in the suture plane to illustrate the flesh coloration, and several stones, all of the subject variety.

DETAILED DESCRIPTION

Referring more specifically to the pomological details of this new and distinct variety of plum tree, the following has been observed under the ecological conditions prevailing at the farm of the H. P. Metzler & Sons Company, located near Del Rey, Calif. All major color code designations are by reference to the Inter-Society Color Council, National Bureau of Standards. Common color names are also occasionally employed.

TREE

Size: Medium, with upright growth.
Figure: Average.
Productivity: Noteworthy.
Regularity of bearing: Excellent.
Trunk:
- *Thickness.*—Average.
- *Surface texture.*—Normal; rough.
- *Color.*—Brown, (62 d. gy Br.).
- *Lenticels.*—Approximately nine through twelve per square inch.

Branches:
- *Size.*—Average.
- *Surface texture.*—Average plum bark, similar to that of the trunk.
- *Color.*—Brown, (62 d. gy Br.).
- *Lenticels.*—Approximately nine through twelve per square inch.

LEAVES

Size: Medium.
- *Length.*—Approximately 3 inches to 3½ inches, (76.2 through 88.9 mm).

*Width.*—Approximately 1 inch to 1½ inches, (25.4 through 38.1 mm).

*Shape.*—Lanceolate.

*Color.*—Dorsal surface — Bright Green (125 M. 01. G.). Ventral surface — Pale Green (122 gy. Y. G.).

*Marginal form.*—Finely serrate.

*Shape of glands.*—Globose; very small in size; on occasion, some leaves have no glands evident.

*Petiole.*—Length — approximately 9/16 inch (14.288 mm); Thickness — approximately 1/16 inch (1.588 mm).

*Stem glands.*—Number — if the stem glands are evident, they will appear as one pair. Arrangement — if the stem glands are evident, they appear as one pair opposite to each other. Size — very small; approximately 1/32 inch, (0.794 mm).

*Stipules.*—None evident.

Flower buds:

*Size.*—Diameter — approximately ⅛ inch, (3.175 mm.); however, the size of the bud is 3/16 inch (4.762mm.) at a time when a white color appears at the apex of the bud.

*Petiole.*—Length — approximately ⅛ inch, (3.175 mm.), this length is determined at a time when no white color appears at the apex of the bud.

*Shape.*—Slightly elongated; buds form in clusters, however, each bud appears to develop by itself.

*Color.*—Dull Green (120 M. Y. G.).

Flowers:

*Date of bloom.*—The last week of February through the first week in March; the date of bloom is somewhat later than the Santa Rosa Plum Tree at Del Rey, Calif.

*Size.*—Petal Width — approximately 3/16 inch, (4.762 mm.); Petal Length — approximately 5/16 inch, (7.938 mm.).

*Color.*—White (#263).

*Stem length.*—Approximately ⅜ inch, (9.525 mm.); this length is determined at the time of full bloom.

*Flower petal form.*—Slightly elongated; the flowers are generally characterized as small, white blossoms.

FRUIT

Maturity when described: For commercial harvesting; approximately Aug. 25 through 28 at Del Rey, Calif.

Size:

*Uniformity.*—Good.

*Axial diameter.*—Approximately 2¼ inches to 2½, (57.14 through 63.5 mm.).

*Diameter transverse in the suture plane.*—Approximately 2¼ inches, (57.15 mm.).

*Diameter transverse in the cheek plane.*—Approximately 2¼ inches through 2½ inches, (57.15 through 63.5 mm.).

Form:

*Uniformity.*—Good.

*Shape.*—It appears almost heart-shaped, and it has a heavy apex point area.

Suture: Smooth and slightly recessed.

*Suture length.*—Approximately 3½ inches, (88.9 mm.); the suture extends from the base to the apex.

Ventral surface: Slight, with a heavy point.

Stem cavity: Elongated.

Base: Rounded and flat.

Apex: Slightly elongated.

Pistil Point: Variable, having a very slight, heavy point, to a heavy round point.

Stem:

*Length.*—Approximately ⅜ inch, (9.525 mm.).

*Width.*—Approximately 1/16 inch, (1.588 mm.).

Skin:

*Thickness.*—Variable, approximately 1/64 inch (0.397 mm), although occasionally a thickness slightly less may be found.

*Texture.*—Skin may appear slightly rough, however it is quite smooth and upon polishing takes on a bright shine.

*Tendency to crack.*—None observed.

*Color.*—A very dark blue (230 blackish).

Flesh:

*Color.*—Yellow (87 m.y.).

*Surface texture of pit well.*—Slightly rough.

*Color of pit well.*—Yellow (88 d.y.).

*Juice production.*—Average; juicy; mild.

*Flavor.*—Mild and sweet, not sharp; there is no indication of any acid taste.

*Aroma.*—Very slight.

*Texture.*—Smooth.

*Fibers.*—None evident.

*Ripening.*—Even.

*Eating quality.*—Noteworthy.

Stone:

*Free or cling.*—Nearly full freestone.

*Fibers.*—None evident.

*Color of stone.*—Brown (94 1. 01. Br.).

*Size of stone.*—Length — approximately 13/16 inch through ⅞ inch, (20.638 mm through 22.225 mm.). Width — approximately 9/16 inch through ¾ inch, (14.288 mm. through 19.050 mm.). Thickness — approximately 5/16 inch, (7.938 mm.).

*Form of stone.*—Elongated.

*Base.*—Round.

*Texture of sides.*—Nearly smooth.

*Ridges.*—None.

Use: Fresh market.

Keeping quality: Excellent, the subject variety has displayed characteristics that it will keep in excess of three weeks in cold storage with no deleterious effects noted.

Shipping quality: Excellent, this fruit remains very firm for extended periods of time and thus should ship very well. All indications are that the fruit does not bruise easily.

Although the new variety of plum tree possesses the described characteristics as a result of the growing conditions in Del Rey, Calif. in the central part of the San Joaquin Valley, it is to be understood that variations of the usual magnitude in characteristics incident to growing conditions, fertilization, pruning and pest control are to be expected.

Having thus described and illustrated my new variety of plum tree, I claim:

1. A new and distinct variety of plum tree substantially as illustrated and described which is distinguished by producing fruit which matures late in the season, approximately Aug. 25 through 28 at Del Rey, Calif., and which bears a dark blue, almost black-colored fruit which is heart-shaped in appearance and has a firm texture which makes the fruit easy to handle and ship, and furthermore which has excellent cold storage characteristics.

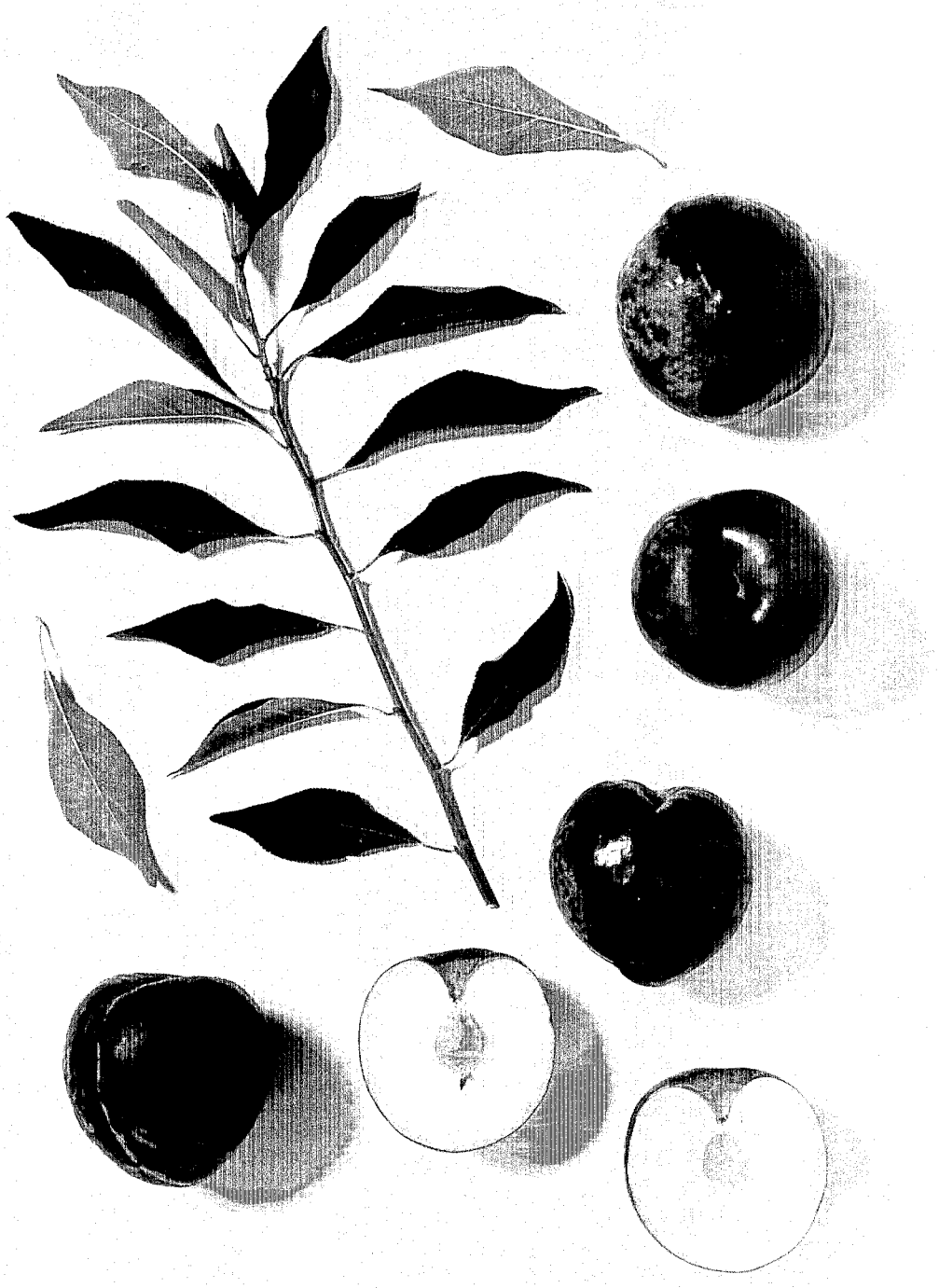

* * * * *